United States Patent [19]

Celmer et al.

[11] 4,081,532

[45] Mar. 28, 1978

[54] POLYCYCLIC ETHER ANTIBIOTIC PRODUCED BY NEW SPECIES OF DACTYLOSPORANGIUM

[75] Inventors: Walter D. Celmer, New London; Walter P. Cullen, East Lyme; Charles E. Moppett, Mystic; John B. Routien, Lyme; Mark T. Jefferson, Waterford, all of Conn.; Riichiro Shibakawa, Handa; Junsuke Tone, Chita, both of Japan

[73] Assignee: Pfizer Inc., New York, N.Y.

[21] Appl. No.: 724,869

[22] Filed: Sep. 20, 1976

[51] Int. Cl.² .................................................. A61K 35/00
[52] U.S. Cl. .................................................. 424/122; 195/81

[58] Field of Search .................................. 424/122; 195/81

[56] References Cited

U.S. PATENT DOCUMENTS 3,989,820  11/1976  Florent et al. .................... 424/122

Primary Examiner—Jerome D. Goldberg
Attorney, Agent, or Firm—Connolly and Hutz

[57] ABSTRACT

A new polycyclic ether antibiotic produced by three strains of a new species of Dactylosporangium under submerged fermentation conditions is useful in controlling coccidiosis in poultry and in improving feed utilization efficiency in ruminants.

8 Claims, 5 Drawing Figures

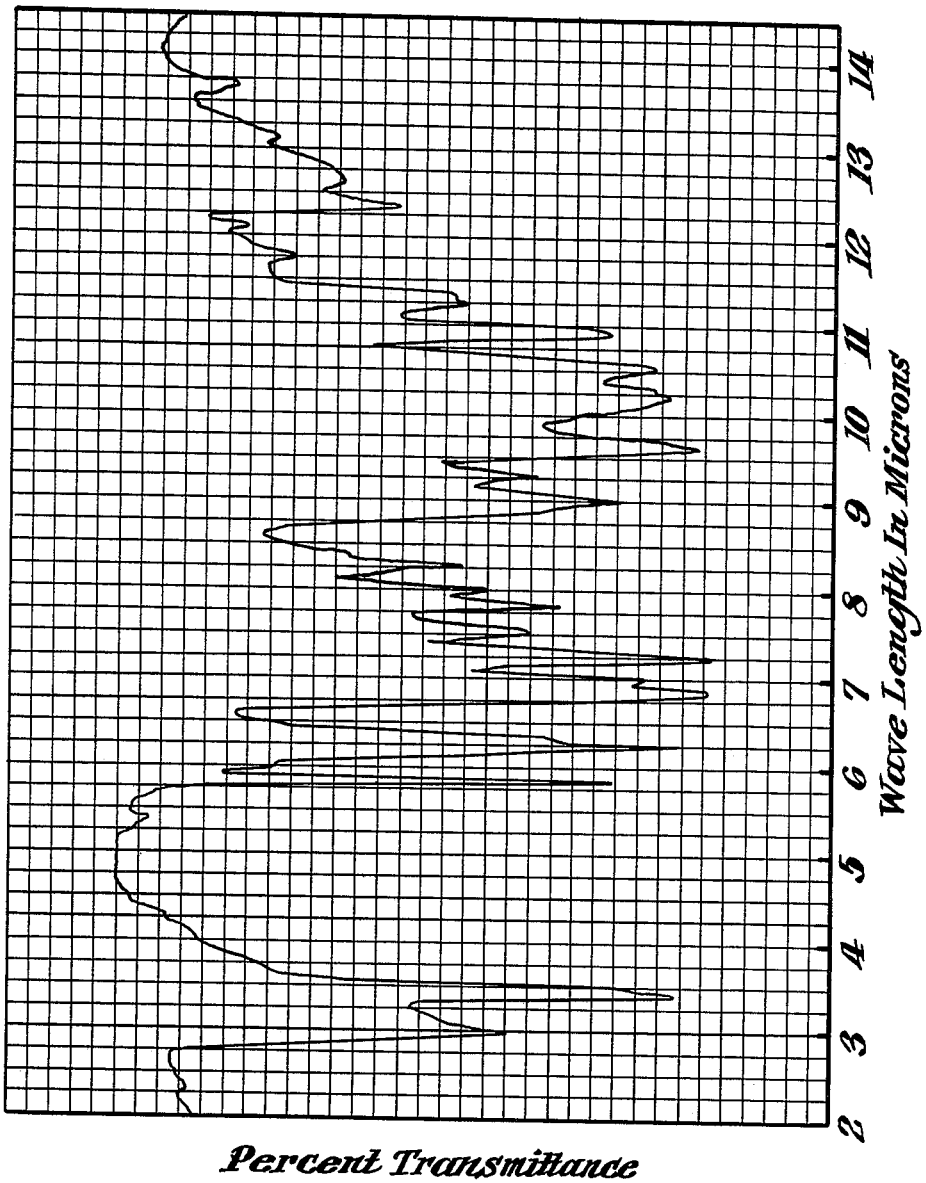
Fig. 2. Infrared Absorption Spectrum of Compound CP44,161 Na Salt

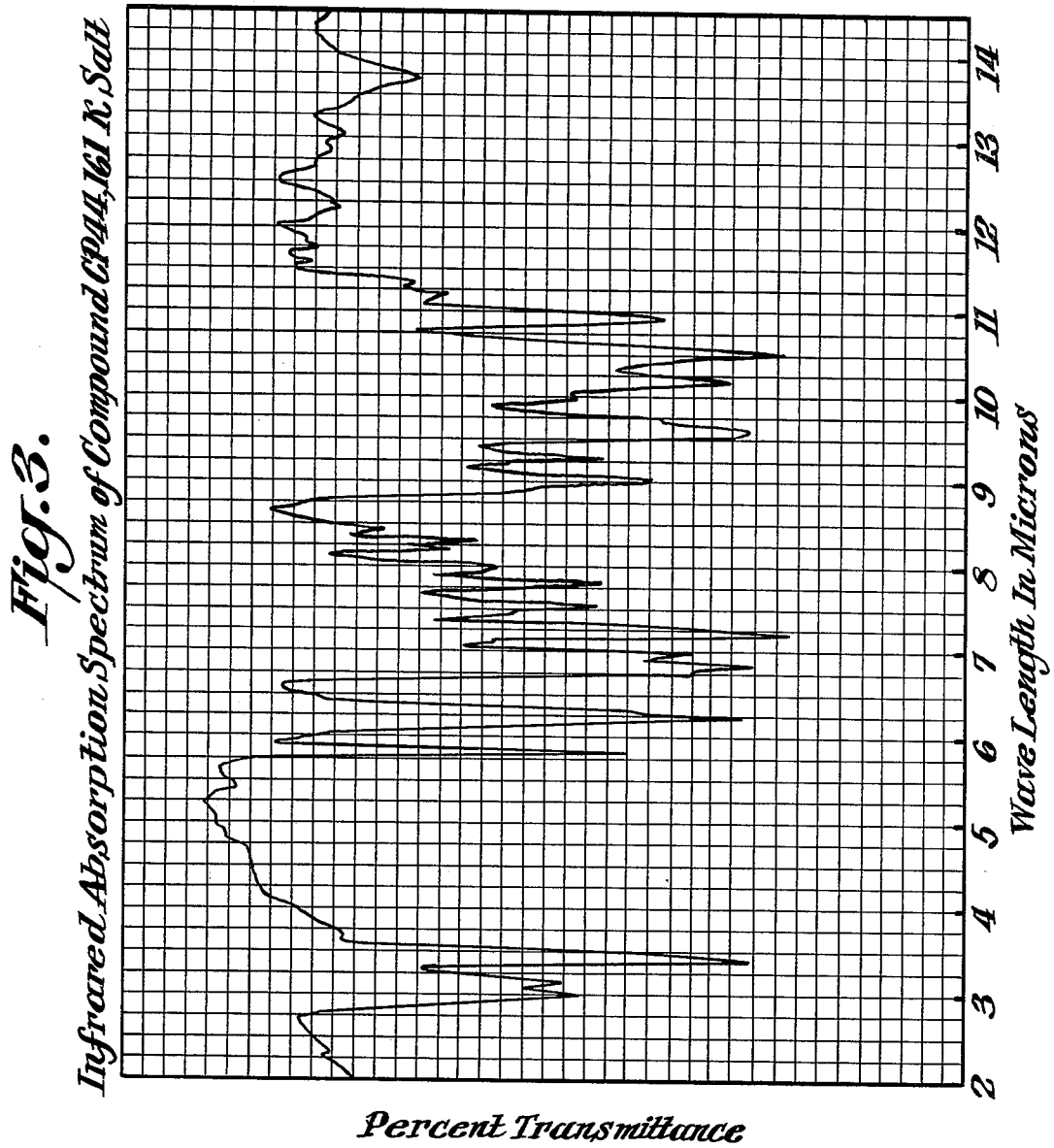

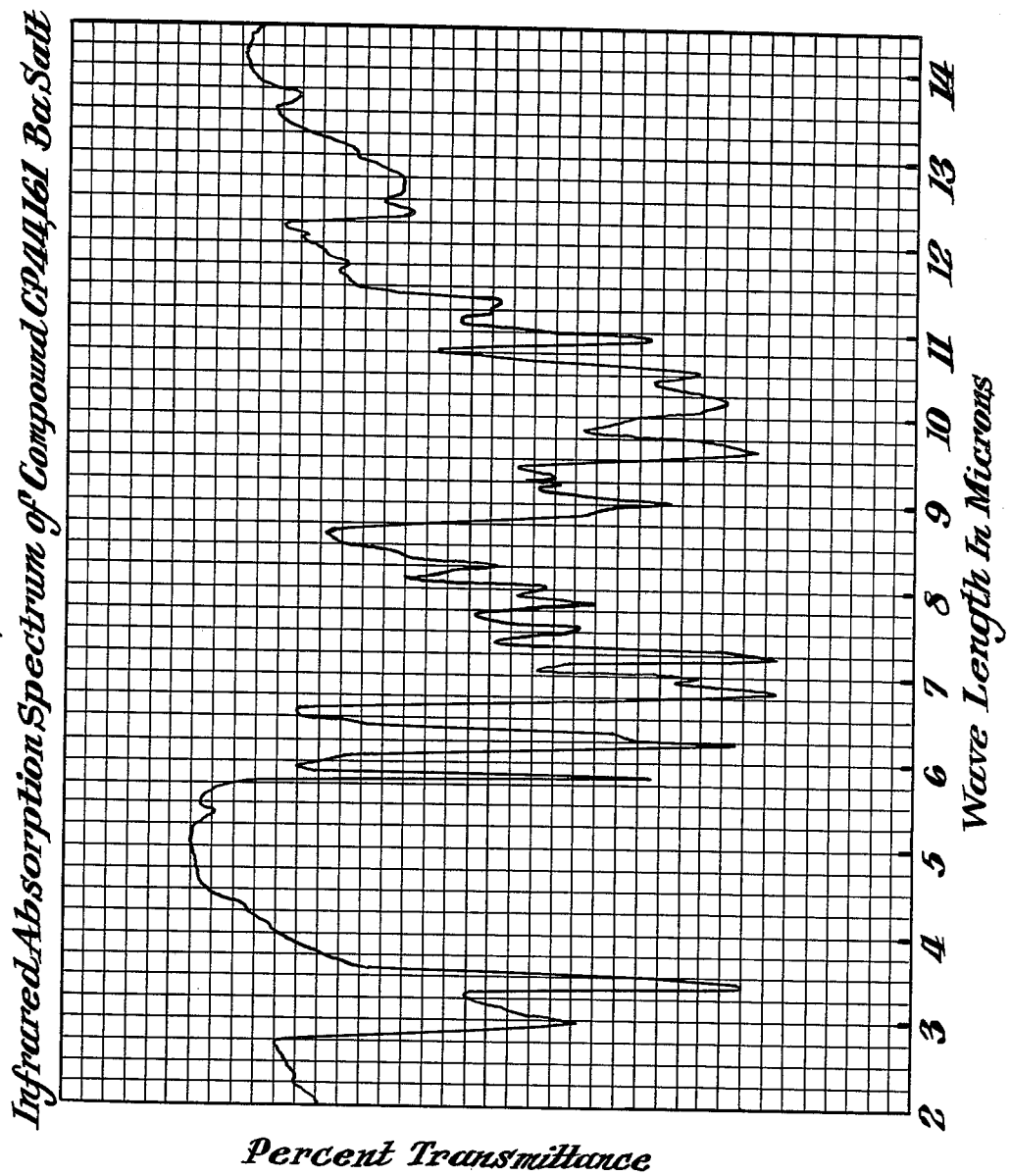

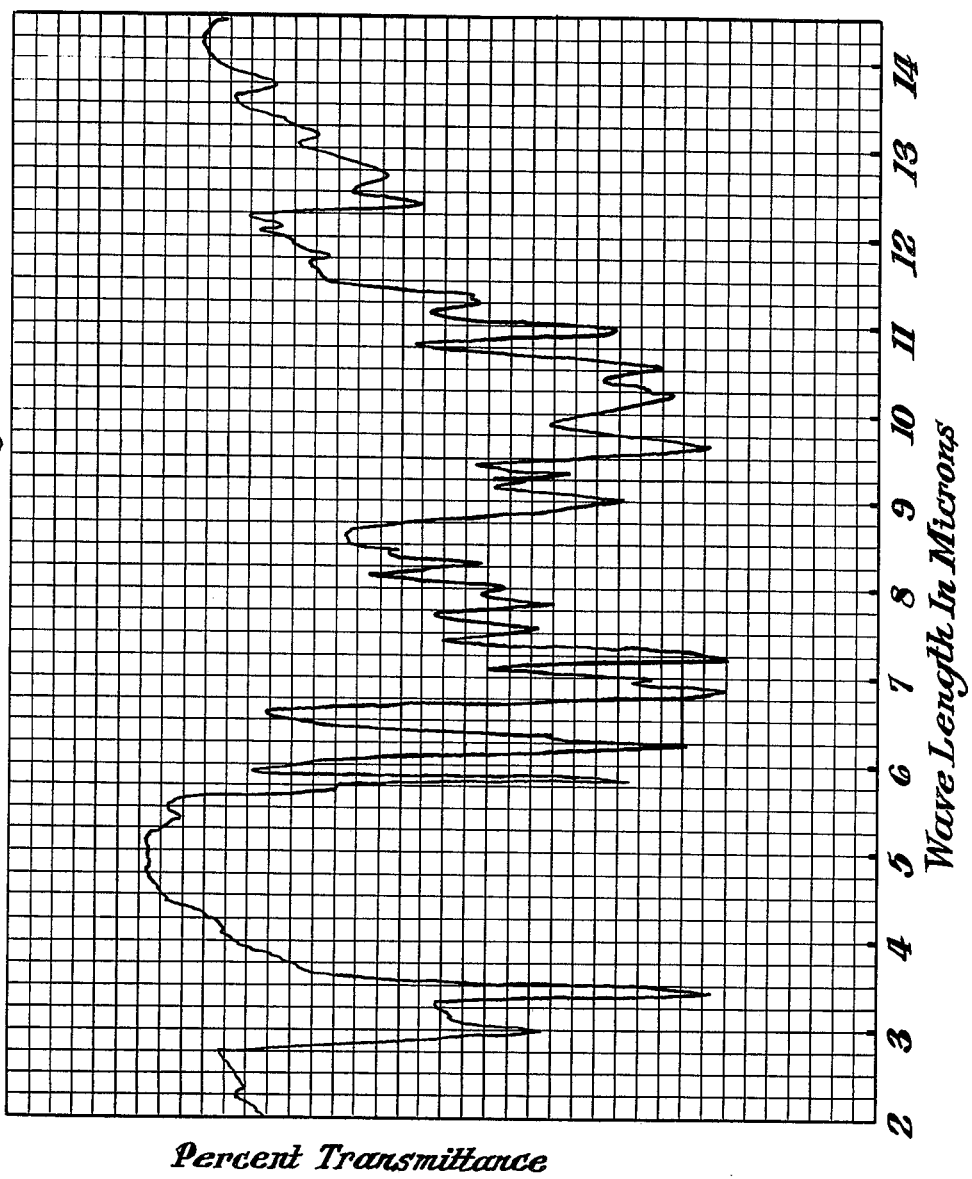
Fig. 5. Infrared Absorption Spectrum of Compound CP-44,161 Ca Salt

POLYCYCLIC ETHER ANTIBIOTIC PRODUCED BY NEW SPECIES OF DACTYLOSPORANGIUM

BACKGROUND OF THE INVENTION

This invention is concerned with a new member of the acidic polycyclic ether group of antibiotics, a class of compounds characterized biologically by their effect on cation transport in mitochondria. This family of antibiotics includes monensin (J. Amer. Chem. Soc., 89:5737, 1967); nigericin (Biochem. Biophys. Res. Comm., 33:29, 1968); grisorixin (J. Chem. Soc. Chem. Commun., 1421, 1970); dianemycin (J. Antibiotics, 22:161, 1969); salinomycin (J. Antibiotics, 27:814, 1974); X-537A (J. Chem. Soc. Chem. Commun., 967, 1972); X-206 (J. Chem. Soc. Chem. Commun., 927, 1971); and A204A (J. Amer. Chem. Soc., 95:3399, 1973).

The polycyclic ether antibiotics listed above are active against Gram-positive bacteria, fungi and protozoa. These antibiotics exhibit potent anticoccidial activity.

The control of coccidiosis continues to be a serious problem to the poultry industry. There are six species of coccidia which produce easily discernible morbidity in susceptible chickens. *Eimeria tenella, E. necatrix, E. brunetti, E. acervulina, E. maxima* and *E. mivati* produce damage either directly through destruction of epithelial cells of the digestive tract or indirectly through production of toxins. Three other species of protozoa belonging to the same genus are considered to be relatively innocuous; however, *E. mitis, E. hagani* and *E. praecox* are capable of reducing weight gain, lowering feed efficiency and adversely affecting egg production.

The polycyclic ether antibiotics possess a high degree of effectiveness against all species of *Eimeria*. These antibiotics can, therefore, be regarded as "broad spectrum" coccidiostats.

SUMMARY OF THE INVENTION

This invention is concerned with a new acidic polycyclic ether antibiotic produced by each of three strains of a new species of *Dactylosporangium* under submerged aerobic conditions in aqueous nutrient media. The antibiotic and its cationic salts are active against a variety of microorganisms, effective in controlling coccidiosis in poultry and act to improve feed utilization efficiency in ruminants.

DETAILED DESCRIPTION OF THE INVENTION

The antibiotic producing microorganisms of the present invention, isolated from soil samples in Japan, were found on examination to have the morphological features of a *Dactylosporangium*. This genus is characterized by dactyliform (finger-like) sporangia, 3-4 motile spores in each sporangium and many large, globose bodies on the substrate mycelium.

The three cultures and a culture of the type species *Dactylosporangium aurantiacum* ATCC 23491, obtained from the American Type Culture Collection, were grown on the media listed in the publication, "Dactylosporangium, gen. nov.," by J. E. Thiemann et al. in Archiv fur Mikrobiologie 58, 42-52 (1967). The cultures failed to grow on the medium described for carbohydrate utilization; culture studies were repeated on the same medium adjusted to pH 7.0 from the described acidic condition.

Preparation of the cultures for planting on media was carried out by the method described in Internat. Jr. System. Bact., 16, 322 (1966). Cultures were incubated at 28° C. except where otherwise noted. Most results were recorded after 14 days of incubation but some were recorded before and after that period of time. The colors were described in ordinary color terms and also by reference to Maerz and Paul's Dictionary of Color, second edition, 1950. The media and references to their composition are as follows:

1. Glucose-Asparagine Agar: Waksman, S.A., The Actinomycetes, Vol. 2, 1961, medium No. 2, p. 328.
2. Glycerol-Asparagine Agar: Ibid, medium No. 3, p. 328.
3. Czapek-Glucose Agar: Ibid, medium No. 1, p. 328.
4. Nutrient Agar: Ibid, medium No. 14, p. 330.
5. Bennett's Agar: Ibid, medium No. 30, p. 331.
6. Oatmeal Agar: ISP No. 3 medium, Difco.
7. Tyrosine Agar: ISP No. 7 medium, Difco.
8. Calcium Malate Agar: Waksman, S.A., Bact. Rev., 21, 1-29, (1957).
9. Gelatin: R. E. Gordon and J. M. Mihm, J. Bact., 73, 15-27 (1957).
10. Starch Agar: Ibid.
11. Potato Plugs: Plugs placed in tubes containing a glass ring at the bottom and about 0.5 ml water and autoclaved at 121° C. for 20 minutes.
12. Carrot Plugs: Procedure same as for Potato Plugs.
13. Organic Nitrate Broth: Waksman, S.A. The Actinomycetes, Vol. 2, 1961, medium 37, p. 332.
14. Dextrose Nitrate Broth: Ibid, medium 1, p. 328 with 3.0 g of dextrose
15. Cellulose: H. L. Jensen, Proc. Linnean Soc. N. S. Wales, 55, 231-248 (1930). M. Levine and H. W. Schoenlein, A Compilation of Culture Media, medium No. 2511 (1930).
16. Casein Agar:
17. Hickey and Tresner's Agar: J. Bact., 64, 891-892 (1952).

The new culture (Pfizer F.D. 25647) was described as follows on the various media:

Glucose — Asparagine Agar — Growth fair, occurring as isolated, slightly raised, smooth colonies, salmon color (9C7); reverse the same color as the surface; no soluble pigment.

Glycerol — Asparagine Agar — Growth poor, consisting of isolated, flat colonies, pale pink (9A3); reverse the same color as the surface; no soluble pigment.

Czapek — Glucose Agar — Growth extremely sparse as a few isolated colonies, very pale salmon color.

Hickey and Tresner's Agar — Growth good, raised and roughened, pinkish orange (near 11F8); reverse similar to the surface in color; no soluble pigment.

Bennett's Agar — Growth moderate, consisting of a wrinkled mass of colonies, orange (near 11D7); reverse similar to the surface in color; no soluble pigment.

Nutrient Agar — Growth poor, consisting of isolated very slightly raised colonies, cream-colored to pale pink (10A2 to 10B2); reverse the same color as the surface; no soluble pigment.

Oatmeal Agar — Growth fair to moderate, consisting of slightly raised colonies, pinkish (near 9B6); reverse the same color as the surface; no soluble pigment.

Casein Agar — Growth poor in form of isolated, slightly raised colonies, pale orange (near 10F8); reverse similar in color to the surface; no soluble pigment.

Calcium Malate Agar — Growth very poor, flat, thin, colorless; no soluble pigment.

tion broth with an organic solvent such as chloroform, ethyl acetate, methylisobutyl ketone or butanol at a pH range of 4.0 to 10.0. A major portion of the antibiotic is contained in the mycelium and may be extracted therefrom by slurrying the separated mycelium with a water-soluble solvent such as methanol. The solvent is concentrated to a thin syrup and the antibiotic precipitated by the addition of hexane or heptane.

The preferred method of separation and recovery of antibiotic Compound 44,161 is as follows: The whole, unfiltered fermentation broth is extracted with about 1/5 to ½ volume of methylisobutyl ketone. The solvent extract is concentrated under vacuum to an oily residue which is then slurried with silica gel $PF_{254}$(buffered at pH 9.0) in heptane and added to a column of pH 9.0 buffered silica gel 60 topped with a layer of pH 9.0 buffered silica gel $PF_{254}$, both types of silica gel available from E. Merck, Darmstadt, Germany. The silica gel column is successively developed with heptane, chloroform:heptane (1:1 v/v), chloroform, chloroform:ethyl acetate (3:1 v/v) and ethyl acetate. The eluate fractions rich in antibiotic Compound 44,161 are combined and evaporated under vacuum to an oily residue which is taken up in ether, treated with activated charcoal (Darco G60), filtered and washed successively with pH 9.0, 4.8 and 3.0 phosphate buffer. Concentration in vacuo followed by trituration with methanol yields crystalline Compound 44,161.

The sodium salt of Compound 44,161 may be prepared by shaking an ether or ethyl acetate solution of the free acid with aqueous sodium carbonate. The potassium salt is prepared in similar fashion. The calcium and barium salts are prepared by treating an ether or ethyl acetate solution of the free acid with aqueous calcium hydroxide and barium hydroxide, respectively.

Compound 44,161 and its salts exhibit excellent activity against coccidiosis infections in poultry. When incorporated in the diet of chickens at a level of 50 to 200 ppm, the compounds are effective in controlling single infections of *Eimeria tenella, E. acervulina, E. maxima,* etc. and mixed infections of these organisms.

Because of its end use for the prevention and treatment of coccidiosis in poultry, whole fermentation broth containing Compound 44,161 may be taken to dryness (preferably by spray-drying) and incorporated in poultry feed at the desired antibiotic potency level.

Compound 44,161 exhibits inhibitory action against the growth of a number of microorganisms (Table I). The test organism is inoculated in a series of test tubes containing nutrient medium and varying concentrations of Compound 44,161 to determine the minimal concentration of the antibiotic in mcg/ml which inhibits the growth of the organism over a period of 24 hours.

Table I

| Organism | | Compound 44,161 (sodium salt) |
|---|---|---|
| *Staphylococcus aureus* | 01A005 | <0.1 |
| | 01A052 | <0.1 |
| | 01A109 | <0.1 |
| | 01A110 | <0.1 |
| | 01A111 | <0.1 |
| | 01A087 | <0.1 |
| | 01A400 | <0.1 |
| *Streptococcus faecalis* | 02A006 | <0.1 |
| *Streptococcus pyogenes* | 02C203 | <0.1 |
| *Mycobacterium smegmatis* | 05A001 | >200 |
| *Bacillus subtilis* | 06A001 | <0.1 |
| *Escherichia coli* | 51A229 | >200 |
| | 51A266 | >200 |
| | 51A125 | >200 |
| *Pseudomonas aeruginosa* | 52A104 | >200 |
| *Klebsiella pneumoniae* | 53A009 | >200 |

Table I-continued

| Organism | | Compound 44,161 (sodium salt) |
|---|---|---|
| | 53A031 | >200 |
| *Proteus mirabilis* | 57C064 | >200 |
| *Salmonella cholerae-suis* | 58B242 | >200 |
| *Pasteurella multocida* | 59A001 | 6.25 |
| *Serratia marcescens* | 63A017 | >200 |
| *Enterobacter aerogenes* | 55A004 | >200 |
| *Neisseria sicca* | 66C000 | 0.2 |

Efficacy data for Compound 44,161 and its salts against coccidiosis infections in chickens were obtained in the following fashion. Groups of 3–5 ten day old SPF white leghorn cockerel chicks were fed a mash diet containing antibiotic Compound 44,161 or its sodium or potassium salt uniformly dispersed therein. After being on this ration for 24 hours each chick was inoculated per os with oocysts of the particular species of Eimeria being tested. Other groups of 3–5 ten day old chicks were fed a similar mash diet free from antibiotic Compound 44,161 or its salts. They were also infected after 24 hours and served as infected controls. Still other groups of 3–5 ten day old chicks were fed the mash diet free of antibiotic Compound 44,161 and were not infected with coccidiosis. These served as normal controls. The results of treatment were evaluated after five days in the case of *E. acervulina,* and six days for all other challenges.

Table II illustrates the results obtained.

Table II

| Species Infection | Dose (ppm) | Ave. degree of infection* | Ratio* | Weight gain (%) |
|---|---|---|---|---|
| *E. tenella* | 100 | 0.3 | 0.09 | 63 |
| | 75 | 1.3 | 0.37 | 82 |
| *E. acervulina* | 125 | 0.4 | 0.22 | 59 |
| | 100 | 0.6 | 0.33 | 51 |
| | 75 | 1.0 | 0.56 | 67 |
| *E. necatrix* | 125 | 0.2 | 0.1 | 77 |
| | 100 | 0.2 | 0.1 | 82 |
| | 75 | 0.2 | 0.1 | 72 |
| *E. maxima* | 125 | 0.4 | 0.22 | 54 |
| | 100 | 0.8 | 0.44 | 49 |
| | 75 | 1.0 | 0.56 | 37 |
| *E. brunetti* | 125 | 0.6 | 0.38 | 57 |
| | 100 | 0.6 | 0.38 | 82 |
| | 75 | 1.4 | 0.88 | 61 |

*The criteria used to measure anticoccidial activity consisted of lesion scores of 0 to 4 for *E. tenella* after J.E. Lynch, A New Method for the Primary Evaluation of Anticoccidial Activity, Am. J. Vet. Res., 22, 324–326 (1961); and 0 to 3 for the other species based on a modification of the scoring system devised by J. Johnson and W.H. Reid, Anticoccidial Drugs, Exp. Parasit., 28, 30–36 (1970). A constant ratio was established by dividing the lesion score of each treated group by the lesion score of the infected control.

The value of animal feeds generally has been determined directly by feeding the animal. G.B. Pat. No. 1,197,826 details an in vitro rumen technique whereby the changes occurring in feeds brought about by microorganisms are measured more readily and with great accuracy in the evaluation of animal feeds. This technique involves the use of an apparatus in which the digestive processes of the animals are conducted and studied in vitro. The animal feeds, rumen inoculum and various growth promotants are introduced into and withdrawn from a laboratory unit under carefully controlled conditions and the changes taking place are studied critically and progressively during the consumption of the feed by the microorganisms. An increase in the propionic acid content in the rumen fluid indicates that a desirable response in overall ruminant performance has been brought about by the growth promotant in the feed composition. The change in propionic acid content is expressed as percent of the propionic acid content found in the control rumen fluid. Long term in vivo feeding studies are used to show a reliable correlation between propionic acid increase in the rumen fluid and improved animal performance.

Rumen fluid is collected from a fistulated cow which is fed on a commercial fattening ration plus hay. The rumen fluid is immediately filtered through cheese cloth, and 10 ml added to a 50 ml conical flask containing 400 mg. of standard substrate (68% corn starch + 17% cellulose + 15% extracted soybean meal), 10 ml of a pH 6.8 buffer and the test compound. The flasks are gassed with oxygen free nitrogen for about two minutes, and incubated in a shaking water bath at 39° C. for about 16 hours. All tests are conducted in triplicate.

After incubation 5 ml of the sample are mixed with 1 ml of 25% metaphosphoric acid. After 10 minutes 0.25 ml of formic acid is added and the mixture centrifuged at 1,500 r.p.m. for 10 minutes. Samples are then analyzed by gas-liquid chromatography by the method of D. W. Kellog in J. Dairy Science 52, 1690 (1969). Peak heights for acetic, propionic and butyric acids are determined for samples from untreated and treated incubation flasks. Results are shown in Table III.

Table III

| Compound | Concentration (μg/ml) | Propionic Acid (%)* |
|---|---|---|
| 44,161 | 25 | 169 |
|  | 10 | 168 |
|  | 5 | 157 |
|  | 1 | 147 |
| Monensin | 25 | 168 |
|  | 10 | 172 |
|  | 5 | 147 |
|  | 1 | 132 |

*Untreated control = 100%

Based on these data, it can be projected that improvement of feed utilization by ruminants such as cattle and sheep and monogastric animals such as horses, pigs and rabbits will be comparable with that obtained by commercially available Monensin, a polycyclic ether antibiotic. Antibiotic Compound 44,161 may be incorporated in feed compositions as the free acid, sodium salt, potassium salt, calcium salt or mixtures thereof. Dried fermentation broth containing antibiotic Compound 44,161 may be incorporated in feed compositions at the desired potency concentration.

EXAMPLE I

A sterile aqueous medium having the following composition was prepared:

| Ingredient | Grams/liter |
|---|---|
| Glucose | 10 |
| Starch | 20 |
| Yeast extract | 5 |
| Enzymatic digest of casein | 5 |
| Dipotassium hydrogen phosphate | 0.5 |
| Meat meal | 5 |
| Cobalt chloride | 0.002 |
| Calcium carbonate | 4 |
| pH 7.1–7.2 | |

Cells from a slant of *Dactylosporangium salmoneum* ATCC 31224 were transferred to a series of 300 ml flasks each containing 50 ml of this sterile medium and shaken on a rotary shaker at 28°–30° C. for 3–4 days. An aliquot of the grown culture, sufficient to provide a 5% v/v inoculum, was transferred to four-liter fermentors each containing two liters of the following sterile medium:

| Ingredient | Grams/liter |
|---|---|
| Glucose | 10 |
| Soy flour | 10 |
| Starch | 10 |
| Enzymatic digest of casein | 10 |
| Calcium carbonate | 1 |
| Cobalt chloride | 0.002 |
| pH 6.6±0.1 | |

The fermentation was conducted at 28°–36° C. with stirring at 1700 revolutions per minute and aeration at 1.5–2 volumes of air per volume of broth per minute until substantial antibiotic activity was obtained (40–60 hours). The whole broth, without pH adjustment, was twice extracted with $\frac{1}{3}$ to $\frac{1}{2}$ volume of methylisobutyl ketone. The separated solvent extracts were combined and concentrated under vacuum to a thin syrup.

EXAMPLE 2

A sterile aqueous medium having the following composition was prepared:

| Ingredient | Grams/liter |
|---|---|
| Glucose | 10 |
| Starch | 20 |
| Yeast extract | 5 |
| Enzymatic digest of casein | 5 |
| Cobalt chloride | 0.002 |
| Calcium carbonate 1 | |
| pH 6.9±0.1 | |

A 1500 gallon fermentor containing 1000 gallons of medium was seeded with a 10% inoculum of *Dactylosporangium salmoneum* ATCC 31224 prepared by the method of Example I. The fermentation was conducted for about 150–170 hours at 30° C. at an aeration rate of one volume of air per volume of broth per minute. The whole broth (1,200 gallons), without pH adjustment, was extracted with 324 gallons of methylisobutyl ketone and separated on a Podbielniak extractor. The solvent was removed in vacuo to afford 2.5 liters of a dark mobile oil.

To 1.25 kilos of the crude extract was added 500 grams of pH 9.0 buffered silica gel $PF_{254}$ (prepared by adding 1 liter of 0.5 M disodium hydrogen phosphate to 1 kilo of silica gel $PF_{254}$ which was then dried at 110° C. overnight following vigorous agitation on a rotary evaporator) and 1 gallon of heptane. The solvent was removed in vacuo and the mobile slurry then added to the top of a bed of filter aid (Super Cel) approximately 1 inch deep, 1 kilo of pH 9.0 buffered silica gel 60 and 2.5 kilos of pH 9.0 buffered silica gel $PF_{254}$ contained within a 32 inch lap filter. The antibiotic was then eluted with 2.5 gallons of heptane, 5 gallons of chloroform:heptane (1:1 v/v), 5 gallons of chloroform, 5 gallons of chloroform:ethyl acetate (3:1 v/v) and 1 gallon of ethyl acetate. Those eluates (primarily chloroform:heptane — 1:1 v/v and chloroform) rich in Compound 44,161 were combined and evaporated in vacuo to afford an oily concentrate which was taken up in ether, treated with activated charcoal (Darco G60), filtered, and washed with one-half volumes of pH 9.0, 4.8 and 3.0 phosphate buffer, respectively. Concentration in vacuo followed by trituration with methanol led to crystalline Compound 44,161 which was collected by filtration, washed with heptane and dried in vacuo overnight at about 50° C. to constant weight. A second crystallization from methanol following treatment with Darco G60 led to material of m.p. 155°–157° C. A total of 25.8 grams of Compound 44,161 was derived from the original 1.25 kilograms of crude extract.

The free acid is soluble in methylene chloride, chloroform, acetone, ethyl acetate and methylisobutyl ketone. It is partially soluble in methanol, and insoluble in heptane and water.

The crystalline acid is characterized by an average composition by weight of 69.24% carbon, 9.12% hydrogen and 21.64% oxygen (by difference); an optical rotation of $\alpha_D = -10°$ (c = 1.0, acetone); ultraviolet absorption maxima in methanol at 246 and 313 nm with $E_1^{1\%}{}_{cm}$ values of 76 and 51, respectively; and when pelleted in KBr, distinguishable bands in the infrared region as shown in FIG. 1 at the following wavelengths in microns: 2.97, 3.44, 5.80, 6.05, 6.18, 6.30, 6.87, 7.09, 7.28, 7.85, 8.07, 8.65, 9.08, 9.63, 10.20, 10.50, 10.94, and 12.33.

The sodium salt of Compound 44,161 was prepared by shaking a solution of 5 grams of the free acid in 200 ml of ethyl acetate with 200 ml of 5% aqueous sodium carbonate. The organic layer was dried over sodium sulfate, evaporated in vacuo and crystallized from heptane, m.p. 181°–182° C. The sodium salt is characterized by an average composition by weight of 67.79% carbon, 8.69% hydrogen; an optical rotation of $\alpha_D = +0.56°$ (c = 1.0, chloroform); ultraviolet absorption maxima in methanol at 243 and 303 nm with $E_1^{1\%}{}_{cm}$ values of 60 and 54, respectively; and when pelleted in KBr, distinguishable bands in the infrared region as shown in FIG. 2 at the following wavelengths in microns: 3.00, 3.40, 5.84, 6.24, 6.85, 7.00, 7.24, 7.60, 7.84, 8.00, 8.28, 9.00, 9.65, 10.55, 10.93 and 12.37.

The potassium salt was prepared in like fashion employing 5% aqueous potassium carbonate in place of sodium carbonate. The salt was recrystallized from heptane, m.p. 206°–207° C. The crystalline potassium salt is characterized by an average composition by weight of 66.54% carbon, 8.58% hydrogen; an optical rotation of $\alpha_D = +27°$ (c = 1.0, chloroform); ultraviolet absorption maxima in methanol at 243 and 305 nm with $E_1^{1\%}{}_{cm}$ values of 59 and 53, respectively; and when pelleted in KBr, distinguishable bands in the infrared region as shown in FIG. 3 at the following wavelengths in microns: 3.00, 3.15, 3.40, 5.82, 6.24, 6.85, 7.22, 7.55, 7.82, 9.05, 9.60, 10.18, 10.50, and 10.93.

The barium salt was prepared by shaking a solution of 2 grams of the free acid in 80 ml of ethyl acetate with an equal volume of barium hydroxide octahydrate in water (prepared by dissolving 2.4 grams of $Ba(OH)_2 \cdot 8H_2O$ in 80 ml of water). The layers were separated and the organic layer was further washed with a fresh solution of barium hydroxide, dried over sodium sulfate and evaporated in vacuo. Recrystallization from aqueous acetone gave the barium salt, m.p. 188° C. The barium salt is characterized by an average composition by weight of 63.67% carbon, 8.11% hydrogen; an optical rotation of $\alpha_D = -2°$ (c = 1.0, chloroform); ultraviolet absorption maxima in methanol at 243 and 306 nm with $E_1^{1\%}{}_{cm}$ values of 60 and 53, respectively; and when pelleted in KBr, distinguishable bands in the infrared region as shown in FIG. 4 at the following wavelengths in microns: 3.00, 3.40, 5.83, 6.23, 6.84, 7.24, 9.00, 9.64, 10.20, 10.54 and 10.94.

The calcium salt was prepared in like fashion employing a saturated solution of calcium hydroxide in place of barium hydroxide. It had a melting point of 174°–175° C. following crystallization from aqueous acetone. The crystalline calcium salt is characterized by an average composition by weight of 67.67% carbon and 8.85% hydrogen; an optical rotation of $\alpha_D = +0.9°$ (c = 1.0, $CHCl_3$); ultraviolet absorption maxima in methanol at 243 and 306 nm with $E_1^{1\%}{}_{cm}$ values of 54 and 48, respectively; and when pelleted in KBr, distinguishable bands in the infrared region as shown in FIG. 5 at the following wavelengths in microns: 3.00, 3.45, 5.84, 6.24, 6.85, 7.25, 7.85, 8.02, 8.30, 9.02, 9.65, 10.23, 10.60, 10.95, 11.25 and 12.40.

EXAMPLE 3

The method of Example 1 is repeated with comparable results employing *Dactylosporangium salmoneum* ATCC 31222 or *Dactylosporangium salmoneum* ATCC 31223. The antibiotic-containing whole fermentation broth is taken to dryness, preferably by spray-drying.

EXAMPLE 4

The fermentation process of Example 1 was scaled up to fermentors containing 13,000 gallons of broth. The fermentation was run at a temperature of 30° C. and aeration rate of a volume of air per volume of broth per minute. Excess foaming was controlled by the addition of soybean oil. The fermentation time was five days with the pH of the whole broth at 5.0 at that time. The whole broth was extracted with a Podbielniak extractor employing 5000 gallons of methylisobutyl ketone per 13,000 gallons of broth. Each 5000 gallon extract was concentrated under vacuum to 12 gallons and this was displaced with methanol. Antibiotic Compound 44,161 precipitated out of the methanol which was used to triturate the gummy solids, fresh solvent being added five times. Following trituration, the slurry was dissolved in acetone, and filtered to remove insolubles. The acetone was concentrated to a small volume and displaced with heptane from which antibiotic Compound 44,161 was allowed to crystallize. The solids were filtered, rinsed, vacuum dried and milled. A total yield of crystalline antibiotic Compound 44,161 as high as 3.45 kilograms was obtained from 13,000 gallons of whole fermentation broth.

What is claimed is:

1. The antibiotic Compound 44,161, or the pharmaceutically acceptable salts thereof, said antibiotic when in the form as the crystalline free acid having a melting point of 155°–157° C.; $\alpha_D = -10°$ at a concentration of 1% in acetone; an average composition by weight of 69.24% carbon, 9.12% hydrogen and 21.64% oxygen (by difference); ultraviolet absorption maxima in methanol at 246 and 313 nm with $E_1^{1\%}{}_{cm}$ values of 76 and 51, respectively; and, when pelleted in KBr, exhibiting characteristic absorption in the infrared region at the following wavelengths in microns: 2.97, 3.44, 5.80, 6.05, 6.18, 6.30, 6.87, 7.09, 7.28, 7.85, 8.07, 8.65, 9.08, 9.63, 10.20, 10.50, 10.94 and 12.33.

2. The antibiotic of claim 1 when in the form as the crystalline sodium salt.

3. The antibiotic of claim 1 when in the form as the crystalline potassium salt.

4. The antibiotic of claim 1 when in the form as the crystalline barium salt.

5. The antibiotic of claim 1 when in the form as the crystalline calcium salt.

6. A process for producing the antibiotic Compound 44,161 which comprises cultivating a strain of *Dactylosporangium salmoneum* Routien sp. nov. selected from the group consisting of ATCC 31222, 31223 and 31224 in an aqueous nutrient medium containing an assimilable source of carbon, nitrogen and inorganic salts under submerged aerobic fermentation conditions until a substantial amount of said antibiotic is obtained.

7. A process as in claim 6 wherein said antibiotic Compound 44,161 is separated from the fermentation medium.

8. A process as in claim 6 wherein the antibiotic-containing whole fermentation broth is taken to dryness.

* * * * *

United States Patent [19]

Cheesman

[11] 4,081,533
[45] Mar. 28, 1978

[54] METHOD OF REDUCING MAMMALIAN FERTILITY AND DRUGS THEREFOR

[75] Inventor: Dean W. Cheesman, Kentfield, Calif.

[73] Assignee: Regents of the University of California, Berkeley, Calif.

[21] Appl. No.: 719,659

[22] Filed: Sep. 1, 1976

[51] Int. Cl.$^2$ .................... A61K 37/00; C07C 103/52
[52] U.S. Cl. .......................... 424/177; 260/112.5 LH
[58] Field of Search .............. 424/177; 260/112.5 LH

[56] References Cited

U.S. PATENT DOCUMENTS 3,883,498  5/1975  Gillessen et al. .................... 424/177
3,915,947  10/1975  Shields .............................. 424/177

Primary Examiner—Delbert R. Phillips
Attorney, Agent, or Firm—Phillips, Moore, Weissenberger, Lempio & Majestic

[57] ABSTRACT

The pre-ovulatory surge of luteinizing hormone from the pituitary gland is selectively suppressed or eliminated by introducing nonapeptide, 8-arginine vasotocin, or the tripeptide, propyl-arginyl-glycinamide, into the subject. Analogs and related peptides also exhibit a similar inhibitory effect. This anovulatory effect in the female, or reduction in spermatogenesis in the male, results in loss of fertility.

17 Claims, No Drawings